United States Patent [19]
Huffman

[11] 4,449,930
[45] May 22, 1984

[54] DENTAL MODEL ARTICULATOR

[75] Inventor: Ronald E. Huffman, Tucson, Ariz.

[73] Assignee: KV33 Corporation, Tucson, Ariz.

[21] Appl. No.: 486,897

[22] Filed: Apr. 20, 1983

Related U.S. Application Data

[63] Continuation-in-part of Ser. No. 261,562, May 7, 1981, Pat. No. 4,382,787.

[51] Int. Cl.³ .............................................. A61C 11/00
[52] U.S. Cl. ......................................... 433/64; 433/60
[58] Field of Search ........................ 433/54, 57, 64, 60

[56] References Cited

U.S. PATENT DOCUMENTS

| | | | |
|---|---|---|---|
| 824,096 | 6/1906 | Crate | 433/55 |
| 3,429,045 | 2/1969 | Anderson et al. | 433/54 |
| 3,466,750 | 9/1969 | Timberlake et al. | 433/54 |

FOREIGN PATENT DOCUMENTS 572850 11/1958 Belgium ............................... 433/64

Primary Examiner—Robert Peshock
Attorney, Agent, or Firm—Cahill, Sutton & Thomas

[57] ABSTRACT

An articulator for casts of a dental model correlates the casts with the condition to be redintegrated throughout a full range of occlusal and masticatory registration. The articulator includes an hinged two part flexible element, each of which parts is a mirror image of the other, or a hinged one part flexible element having like opposing halves. Each opposed end of either type of element supports a sphere to be positioned within a respective one of a cavity formed in each cast and adhesively secured thereto after alignment of the paired casts. Simulation and tracing the paths of natural occlusal and masticatory registration is effected by pivotal movement about the hinge line and flexing of the articulator.

35 Claims, 8 Drawing Figures

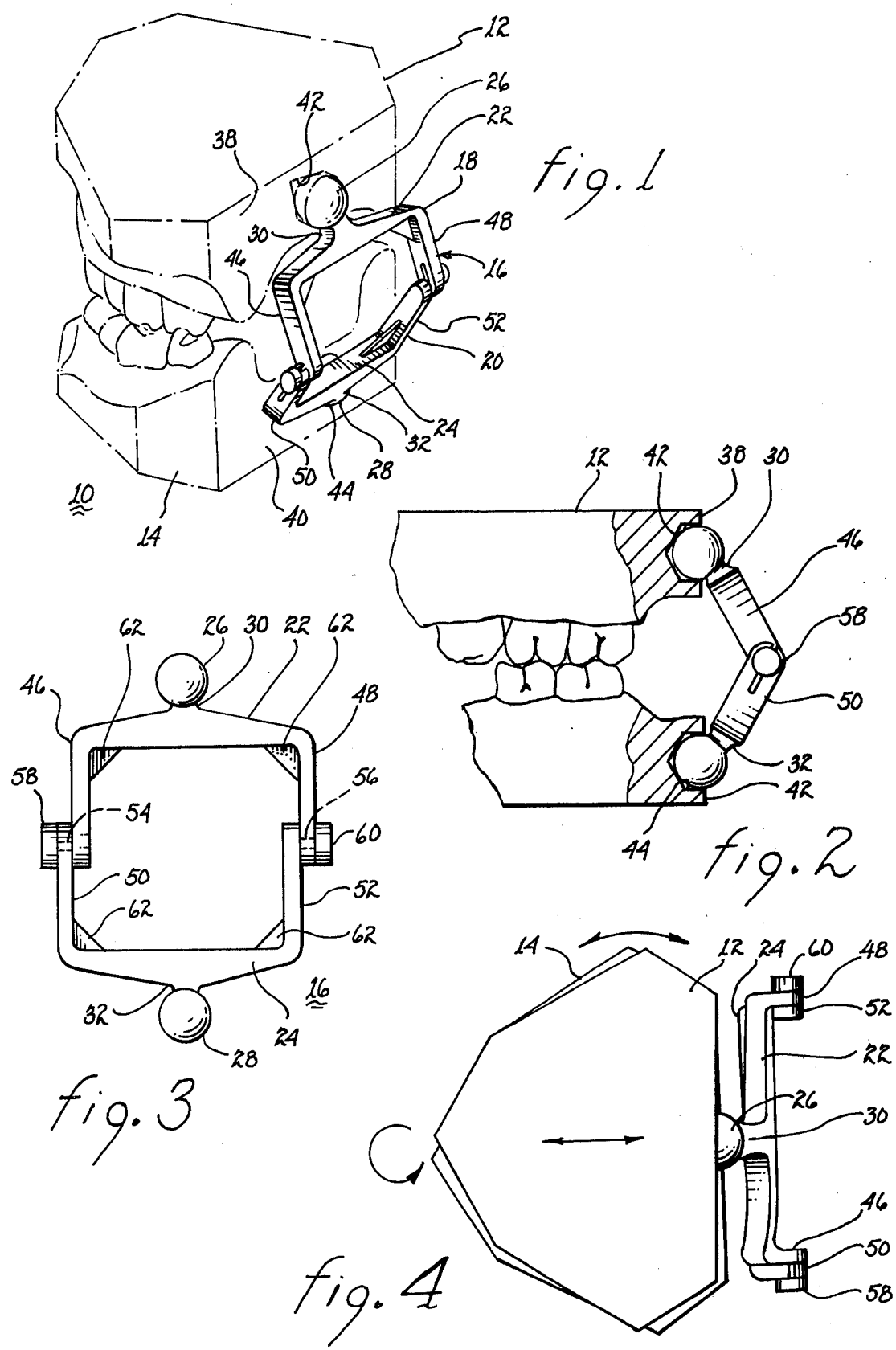

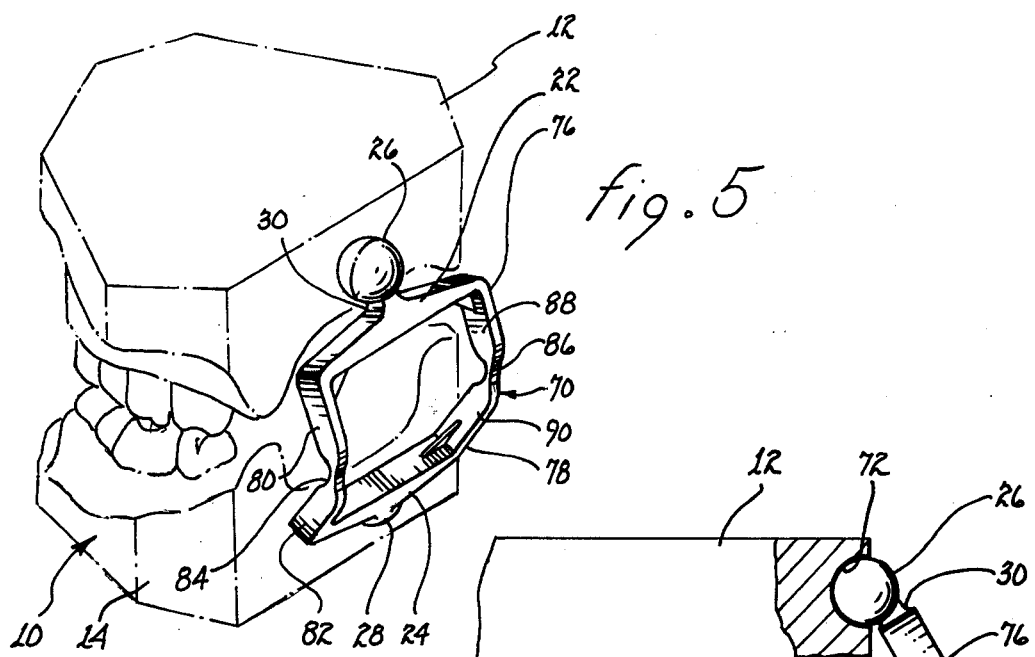
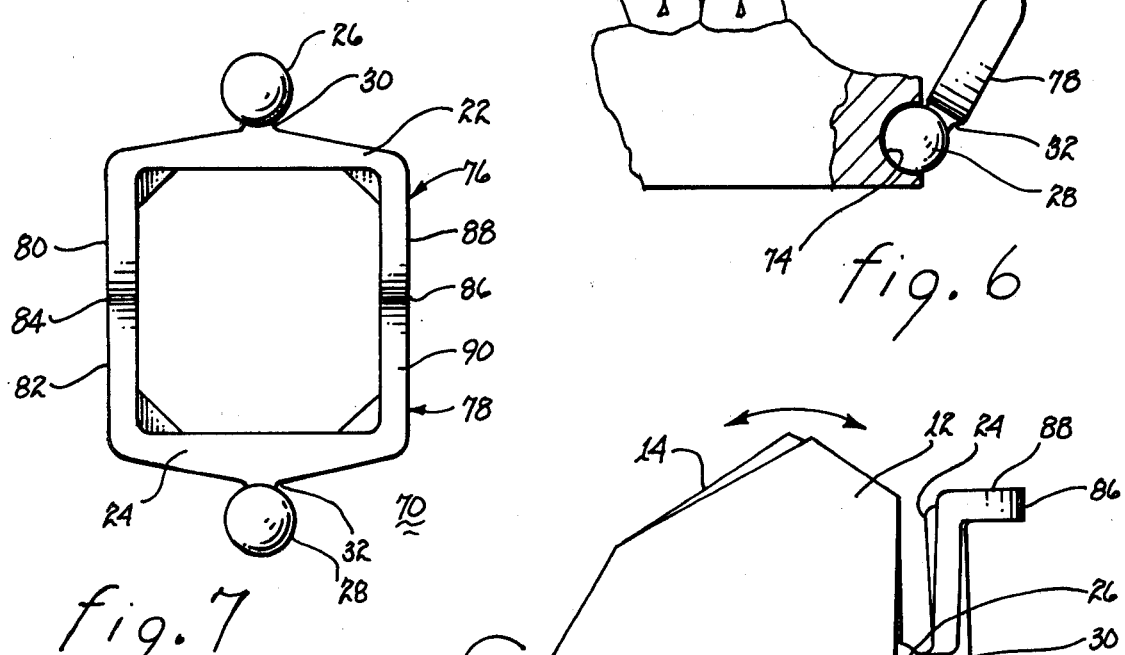
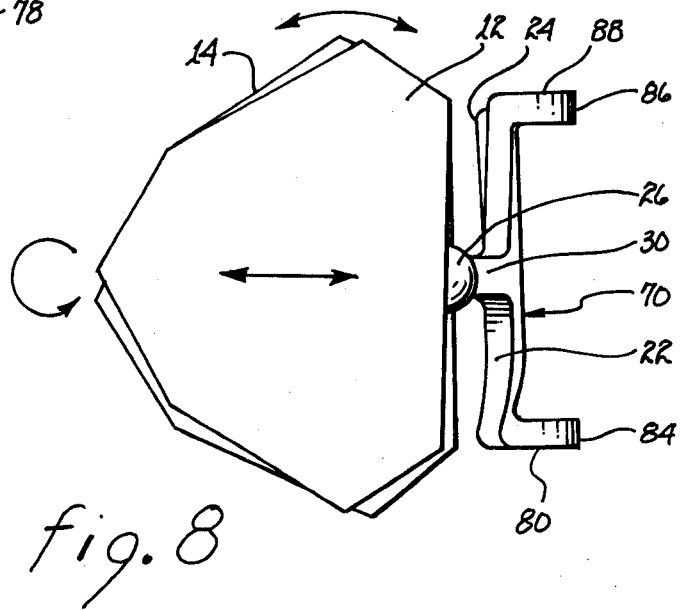

DENTAL MODEL ARTICULATOR

The present application is a continuation-in-part application of a copending application entitled "DENTAL MODEL ARTICULATOR", Ser. No. 261,562, filed May 7, 1981, now U.S. Pat. No. 4,382,787, issued 5/10/83 assigned to the present assignee and describing an invention by the present inventor.

Correlators or articulators for use with casts of a dental model to develop prosthetic dentures or denture elements have been used for a number of years. These articulators range from a very simple device affording only fixed pivotal movement between a pair of casts to highly sophisticated and mechanically complex devices which are capable of simulating the full range of occlusal and masticatory registration unique to any patient. The relatively simple devices are generally inadequate to provide sufficiently accurately registered prosthetic restoration to avoid extensive visits with a dentist to obtain adjustments thereof while the very complex devices are time consuming to operate and require extensive training to use properly. In either situation, the costs incurred to the patient are substantial. Moreover, none of the prior art articulators permit disengagement of the casts from registration with one another without extensive realignment upon reengagement. Thus, a technician is usually forced to perform his work while the casts are mounted on the articulator. Such an environment is difficult to work in with speed and accuracy.

Each of the following listed United States patents are directed to dental articulators which incorporate lockable ball and socket elements to afford pivotal movement and extensible members to afford translational movement: Nos. 175,046, 530,524, 537,812, 565,326, 981,430, 1,736,006, 1,841,728, 2,571,280, 2,600,899, 2,608,762, 2,621,407, 2,765,533, 4,169,314, 4,196,518 and Belgian Patent No. 572,850.

An articulator which provides structure to effect a simple hinged movement without provision of mechanical structure for defining translatory movement or multi-axis pivotal movement is disclosed in U.S. Pat. No. 2,430,177. Simulation of the full range of occlusal and masticatory registration is obtained by resiliently flexing the articulator. Such resiliency is afforded by the coil spring like configuration of a wire element defining each leg of two pairs of legs. For a well trained and experienced technician, the freedom of movement afforded by this articulator is sufficient to permit the formation and adjustments of most prosthetic dentures. Accurate use of the device is predicated upon the formation within each cast of a dental model elongated sockets for receiving, capturing and retaining each of the four wire legs. The casts usually vary in overall physical size, depending upon the size of the patient's teeth to be simulated and the size and configuration of the base formed. To employ the articulator described in this patent, uniformity of spacing between the pairs of sockets in each pair of casts is of paramount importance. The demands imposed by such uniform spacing during formation of the casts is time consuming and requires an experienced technician. No adjustment capability exists within the articulator itself to accommodate differences in spacing, as would be expected as the size of pairs of casts vary in proportion to the physical size of the patient's jaws and the usually uniquely sized bases therefor. Other U.S. Pats. describing articulators include Nos. 824,096, 3,429,045 and 3,466,750.

The present invention is directed to an inexpensive throw away articulator for dental models. The articulator includes a pair of brackets of flexible resilient material interconnected by snap fit hinges. Alternatively, the pair of brackets may be formed as a single unit interconnected by a flexible membrane serving as a hinge to provide pivotal movement between the brackets. A sphere is disposed at opposed ends of each pair of brackets. Each of these spheres is locatable in one of a cavity formed in the rear surface of each cast. Upon alignment of the casts with one another and development of the respective cavities, each sphere is adhesively attached within its respective cavity and the casts become hingedly attached to one another through the pair of brackets. Simulation of the full range of natural occlusal and masticatory registration is effected by a combination of pivotal movement about the hinge line and flexing of the respective brackets. Use of the snap fit hinge embodiment permits rapid disassembly and reassembly without the need of realignment to effect proper registration between the casts; accordingly, a technician can readily perform his work on the casts or dental restoration in comfort by placing the cast to be worked upon on a work surface or in a holder.

A primary object of the present invention is to provide apparatus for operatively simulating the occlusal and masticatory relationships to be redintegrated.

Another object of the present invention is to provide apparatus for mounting and adjustably holding casts of a dental model to simulate their natural registration to facilitate precise occlusal and masticatory correlation of a dental restoration.

Still another object of the present invention is to provide apparatus for resiliently associating operatively interconnecting spaced dental model casts for relative adjustment thereof throughout the range of a full spherical orbit.

Yet another object of the present invention is to provide a manipulatable apparatus to check, trace, fit and polish a dental restoration upon a dental model against and for occlusal and masticatory registration.

A further object of the present invention is to provide an articulator for dental models which is simple and inexpensive to manufacture and operable thoughout a wide range of relative adjustments.

A still further object of the present invention is to provide a throw-away articulator readily attachable to paired dental model casts within a wide range of alignment therebetween.

A yet further object of the present invention is to provide a two piece dental articulator, the two pieces of which are mirror images of one another.

A yet further object of the present invention is to provide a one piece dental articulator.

A yet further object of the present invention is to provide an articulator for supporting a pair of casts which articulator can be disassembled by disengaging snap fit pivots and assembled without need for realignment of the casts by engaging the snap fit pivots.

A yet further object of the present invention is to provide an articulator which is rapidly attachable to support a pair of casts in registration.

A yet further object of the present invention is to provide an articulator which permits a technician to work on a cast physically independent of the other cast without affecting registration therebetween on reassembly of the articulator.

A yet further object of the present invention is to provide a simple method for attaching an articulator to a pair of aligned casts of a dental model.

These and other objects of the present invention will become apparent to those skilled in the art as the description thereof proceeds.

The present invention may be described with greater specificity and clarity with reference to the following drawings, in which:

FIG. 1 is a perspective view illustrating the articulator supporting a pair of casts of a dental model;

FIG. 2 is a partial cross-sectional view illustrating the elements of the articulator;

FIG. 3 illustrates the interconnected elements of the articulator;

FIG. 4 is a partial top view of a mounted articulator illustrating the flexibility of the articulator;

FIG. 5 is a perspective view illustrating a variant of the articulator supporting a pair of casts of a dental model;

FIG. 6 is a partial cross-sectional view illustrating the elements of the variant;

FIG. 7 illustrates the variant; and

FIG. 8 is a top view illustrating the flexibility of the variant.

In the practice of prosthetic dentistry, one very important technical problem is the shaping and fitting of the restoration occlusal surfaces to register, meet and operatively cooperate with opposed surfaces in conformity with the established habits, idiosyncrasies and tooth facet inclinations of the user. The many factors peculiar to the individual have heretofore made proper operative correlation of the restoration with the associated dental elements almost invariably a matter susceptible of satisfactory resolution only through repetitious adjustments and modifications had in the dental chair after installation of the restoration. This occurs despite the use of fixed, even though adjustable, mechanically simulated axes of articulation, planes and arcs of occlusion, lines, planes and axes of symmetry and the like which fail to provide the full orbital range necessary for reconstitution of the natural dental relationships determinable from the traces and indices upon and established through use of the original dentures. To facilitate attainment of the desired operative registration between restorations and their associated dental elements and thereby largely obviate the necessity for adjustments and corrections in the dental chair, the present invention provides a device for laboratory use wherein the relationships to be redintegrated can be fully and accurately portrayed and operatively duplicated as a check mounting for the restoration.

The present invention is a device which hingedly, yieldably and separably associates for registration a pair of casts of a dental model in spaced opposition and which provides relative manipulation of the casts throughout a full spherical orbit wherein every phase and condition of dental occlusive attitude may be exemplified.

In practice, the casts of both the upper and lower natural dentures along with the conditions thereof requiring restoration or correction are made by well known techniques. The casts are secured to the present invention to register in simulation of the natural relationships they portray when in spaced substantially parallel relationship at one limit of the range of relative movement, which position is determinable by the structure of the invention. Through the novel features, structure and characteristics of the invention correlating the restoration or correction and the facet disposition and inclination thereof with the operative range and pattern of movement of the original dentures becomes possible.

Referring to FIG. 1, there is shown a complete dental model 10 having a pair of mating dental model casts 12 and 14 simulative of the original dentures and the condition requiring restoration or correction. An articulator 16 is attached to the casts to maintain them positionally simulative of the natural relationships portrayed when substantially in parallel relationship at one limit of the range of relative movement. A pair of interconnecting elements or brackets 18 and 20 are pivotally attached to one another and are of resilient flexible material sufficient to accommodate relative movement about all axis and within all planes between the casts in simulation of the operative range and pattern of the original dentures.

Referring jointly to FIGS. 1-4, further details of articulator 16 will be described. Each of brackets 18 and 20 includes a base member (22, 24), each of which base members supports a sphere (26, 28). Each sphere may extend directly from its respective bracket or one or both of the spheres may be supported upon a stalk (30, 32) extending from its respective bracket. Brackets 18 and 20 are pivotally joined to one another by pivot means 34, 36; preferably, the pivot means is of the snap fit type.

To mount articulator 16, a mounting defined by a cylindrical cavity, such as formed by a conventional drill bit, or a partial spherical cavity, such as is formed by a ball burr, is developed in rear faces 38, 40 of casts 12, 14, respectively. Spheres 26 and 28 are located within their respective cavities 42, 44 upon angular adjustment about the pivot axis of the respective brackets to obtain the requisite spatial relationship therebetween; nominally, the brackets define an interior obtuse angle. It may be appreciated that the combination of sphere and cavity serves in the nature of a pivot mechanism which provides pivotal freedom between each cast and its connected bracket about any axis of a set of intersecting orthogonal axis prior to setting the relationship therebetween. To maintain the casts in the predetermined fixed spatial relationship to one another at one limit of the range of relative movement, an adhesive is applied intermediate the spheres and their respective cavities to fixedly secure the respective bracket in fixed angular orientation with respect to the casts. Pivotal movement of the casts is effected by relative angular displacement between the joined brackets about the respective pivot means or hinge line. Translational movement in any plane and rotational movement about any axis of the casts with respect to one another is accommodated by the flexibility of brackets 16 and 18 (as shown in dashed lines in FIG. 4).

With the above general understanding of the basic function and structure of the invention, it may be beneficial to review and analyze certain nuances of the invention which render it of great practical benefit in the field of dental correction and restoration.

During initial alignment of the casts, they are maintained in a predetermined relationship sufficient for a technician to draw a line across rear faces 38, 40 of the casts 12, 14 perpendicular to the pivot axis of the casts and generally centered at the rear faces. Thereafter, cavities 42, 44, centered upon the line drawn, are formed in the rear faces by conventional tools. The casts are then again brought into registration to simulate the natural relationships they portray when in spaced substantially parallel relationship at one limit of the range of relative movement. Upon achievement of such orientation of the casts, an adhesive, such as any one of the commercially available fast setting cyanoacrylate or anerobic adhesives, may be employed to secure each sphere within its respective cavity. The articulator now becomes mounted and the casts are correctly positioned relative to one another.

Articulator 16 is formed of a pair of mirror image brackets, each of which includes a base member (22, 24) and a pair of arms (46, 48 and 50, 52). Each base member supports a sphere, which sphere may be, but is not necessarily, located laterally offset of the longitudinal axis of its respective base member and off center along the longitudinal axis such that upon mating of the brackets, a line drawn through the center of the spheres is orthogonal to a line representative of the pivot axis of the articulator. As illustrated, the lateral offset and/or displacement from the base member of each sphere may be effected by a supporting stalk (30, 32). Such stalk also has the further benefit of increasing the distance between the respective base member and the rear face of the attached cast to prevent interference therebetween on attachment and use of the articulator.

The arms of each bracket may be formed to include complementary elements to establish the pivot means. In example, one arm may include a slot terminating in a circular bearing surface while the other arm may include a pin extending therefrom for retentative engagement with a corresponding slot and bearing surface. The pin, molded or otherwise formed upon fabrication of each of brackets may be a simple shaft (54, 56) extending therefrom and terminated by an end plate (58, 60). The space intermediate the arm and end plate is generally equivalent to the width of the arm to be disposed therebetween into slotted retention with the shaft. Alternatively, each arm may include an aperture penetrably engageable by ancillary pin means or the like. Webs 62 or other strengthening means may be employed at the interconnection between the base member and the extending arms to provide the requisite strength, yet minimize the mass and size of the articulator.

Preferably, the pivot means is of the snap fit type such that disengagement and reengagement of the brackets (and the supported casts) may be readily effected. Upon reengagement, the casts will be in registration with one another as no adjustments or parameters affecting registration are disturbed by disengagement/reengagement of the pivot means.

A variant 70 of articulator 16 is illustrated in FIGS. 5-8. Herein, cavities 72, 74 are depicted as semispherical rather than cylindrical; it is to be understood that the cavities for either articulator 16 or variant 70 may be spherical, cylindrical or of other configuration. The major structural difference between articulator 16 and variant 70 is couched in the pivot means interconnecting brackets 76, 78 of the variant and forming the hinge therebetween. For uniformity, all reference numerals referring to like elements of articulator 16 will be retained. Arm 80 of bracket 76 is interconnected with corresponding arm 82 of bracket 78 through a flexible resilient membrane 84 formed as part of the arms of the brackets. A similar flexible membrane 86 interconnects arms 88, 90 of brackets 76, 78. As noted above, each of the brackets are of flexible resilient material to permit manipulation of the casts through every phase and condition of dental occlusive attitude. And, the membranes, being of substantially reduced thickness than the interconnected arms, serve in the nature of a hinge to permit pivotal movement of the brackets and attached casts relative to one another. Such pivotal movement is necessary to expose the mounted tooth dies for work thereupon by a dental technician.

One bracket is not offset from the other bracket in variant 70 in the manner the brackets of articulator 16 are offset due to the difference in pivot means; thereby, each sphere 26, 28 of variant 70 may be centered along the longitudinal axis of base members 22, 24 (unlike articulator 16) as well as being centered upon a centerline of the variant (like articulator 16). The spheres may be located lateral of and/or displaced from the respective base member longitudinal axis directly or by means of an interconnecting stalk (30, 32) (like articulator 16). It also follows that brackets 76, 78 on either side of an imaginary plane passing through or traversing membranes 84, 86 are mirror images of one another.

In operation, the mounted casts may be relatively approached, separated, traversed, protruded, retracted, inclined and rotated through every possible condition and position of occlusal and masticatory registration, as shown by the arrows in FIGS. 4 and 8, by simple manipulation to flex the brackets of the articulator. The resiliently yieldable brackets accommodate all deviation from the initial position of the casts to the extent necessary to fully manifest the operative variations of position inherent in the natural dentures.

After fabrication of a restoration and fitting of same to the appropriate cast, the casts may be manipulated to trace the normal occlusal registration of the dentures as determined by the facet inclinations of the natural teeth and the operative correlation of the restoration with the condition to be redintegrated may be checked for correction and precise fitting. The restoration may be removed from the respective cast with or without physical severance of the casts from one another (if articulator 16 is used). By severing the brackets from one another at the pivot means, the casts readily become physically separated from one another and work on the restoration may become more facile. On completion of the work, the casts are rejoined to one another by rejoining the brackets at the pivot means. The severance capability, without an accompanying obligation or requirement to realign or even check the alignment of the casts, is of immense importance to the dental technician's efficiency. After severance, each cast may be worked on physically independent of the other and positioned upon or retained by a work surface which surface can support the cast at an orientation most favorable for the type and nature of the work to be done. And, a check of the accuracy of the work can be made in a matter of seconds by simply snapping the elements of the pivot means together to engage the two brackets with one another and then simulate and trace the paths of natural and masticatory registration.

When variant 70 is employed, the casts can be pivoted 180° apart to permit facile access by a technician to either cast. The extent of rotation is of course, a function of the geometry and angular orientation of the brackets and the flex parameter of the hinging membranes.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A method for mounting casts of a dental model to afford correlation of the casts throughout a full range of occlusal and masticatory registration, said method comprising the steps of:
   (a) pivoting along a pivot axis one end of a first bracket with a hingedly connected one end of a second bracket;
   (b) interconnecting the other end of one of the brackets through a pivot mechanism providing pivotal freedom between each cast and its connected bracket about any axis of a set of intersecting orthogonal axis;
   (c) positioning the casts relative to one another at one end of the range of occlusal and masticatory registration to be redintegrated by adjusting the angular relationship about any or all pivot axis between each cast and its engaged bracket and by adjusting the angular relationship about the pivot axis between the hingedly connected ends of the brackets; and
   (d) immobilizing the angular relationship between each cast and its engaged bracket on completion of said positioning step to maintain permanently fixed the angular relationship between each cast and its respective bracket.

2. The method as set forth in claim 1 wherein said step of pivoting includes the step of disengageably snap fitting the brackets to one another.

3. The method as set forth in claim 1 wherein said step of pivoting includes the step of pivotally connecting the brackets to one another at two discrete locations disposed along a common pivot axis.

4. The method as set forth in claim 3 wherein said step of pivoting includes the steps of disengageably snap fitting the brackets to one another at each of the two discrete locations.

5. The method as set forth in claim 1 wherein each cast includes one element of a ball and socket joint and wherein another element of the ball and socket joint is disposed at the other end of each bracket and wherein said step of interconnecting comprises the steps of interconnecting one and the other elements to form a ball and socket joint between each cast and its attached bracket.

6. The method as set forth in claim 5 wherein the one element comprises a socket and wherein the other element comprises a ball and wherein said step of interconnecting comprises the step of inserting each ball into one of the sockets.

7. The method as set forth in claim 6 wherein said step of pivoting includes the step of pivotally connecting the brackets to one another at two discrete locations disposed along a common pivot axis.

8. The method as set forth in claim 7 wherein said step of pivoting includes the steps of disengageably snap fitting the brackets to one another at each of the two discrete locations.

9. A method for redintegrating the casts of a dental model throughout a full range of occlusal and masticatory registration to develop a dental prosthetic device mounted on the casts, said method comprising the steps of:
   (a) forming a mounting at each cast;
   (b) pivoting along a pivot axis one end of a first bracket with a hingedly connected one end of a second bracket;
   (c) interconnecting each mounting with the other end of one of the brackets through a ball and socket joint;
   (d) positioning the casts relative to one another at one end of the range of occlusal and masticatory registration to be redintegrated by adjusting the angular relationship between each mounting and its engaged bracket and adjusting the angular relationship about the pivot axis between the hingedly connected ends of the brackets;
   (e) immobilizing the ball and socket joint between connected ones of the mounting and the brackets to maintain permanently the fixed angular relationship established between connected ones of the mountings and brackets on completion of said step of positioning;
   (f) flexing the brackets to translate and rotate the casts relative to one another to determine adjustments necessary to the model teeth or prosthetic devices or restorations formed thereon;
   (g) alternatively pivoting the casts about the pivot axis of the brackets through an obtuse angle or disengaging the brackets one from the other to permit unrestricted access to the casts for making the adjustments determined in said flexing step;
   (h) alternatively repivoting the casts into registration with one another or reengaging the brackets with one another depending upon whether said pivoting or disengaging step, respectively, were undertaken; and
   (i) repeating said steps of flexing, alternatively pivoting or disengaging and alternatively repivoting or reengaging until the model teeth, prosthetic device or restoration is developed.

10. The method as set forth in claim 9 wherein the brackets are connected to one another by pivoting snap fits and said steps of disengaging and reengaging comprise the steps of unsnapping and snapping, respectively, the snap fits.

11. An articulator for correlating the casts of a dental model, each of the casts including a mounting, said articulator comprising in combination:
   (a) pair of resiliently flexible brackets, each said bracket terminating at one end;
   (b) means for pivoting the one end of one bracket with the one end of the other bracket about a common pivot axis; and
   (c) means for interconnecting each of the casts with another end of one bracket of said pair of brackets, said interconnecting means including a ball and socket joint wherein one of the ball and socket of said ball and socket joint is defined by the mounting and wherein the other of the ball and socket of said ball and socket joint is formed by said bracket; whereby, the angular relationship between each cast and the interconnected one of said pair of brackets may be fixed after registration of the casts relative to one another by adjusting the angular relationship between each mounting and its engaged one of said pair of brackets and by adjusting the angular relationship about the pivot axis between the pivotally connected ends of said pair of brackets.

12. The articulator as set forth in claim 11 including fixing means disposed intermediate the ball and socket of each said ball and socket joint for fixing the angular relationship therebetween.

13. The articulator as set forth in claim 11 wherein said ball of said ball and socket joint attendant each bracket of said pair of brackets extends from said bracket for engagement with the mounting developed as a socket in the respective cast.

14. The articulator as set forth in claim 11 wherein said pair of brackets are configured as mirror images of one another.

15. The articulator as set forth in claim 11 wherein said pivoting means attendant said brackets is formed as an integral part of said brackets.

16. The articulator as set forth in claim 15 wherein said pair of brackets and said pivoting means are formed as an integral one part unit.

17. The articulator as set forth in claim 11 wherein said interconnecting means includes one of said elements being formed as an integral part of each one of said pair of brackets.

18. The articulator as set forth in claim 17 wherein said pivoting means attendant said brackets is formed as an integral part of said brackets.

19. The articulator as set forth in claim 18 wherein said pair of brackets and said pivoting means are formed as an integral one part unit.

20. The articulator as set forth in claim 18 wherein said pair of brackets are configured as mirror images of one another.

21. The articulator as set forth in claim 20 wherein each bracket of said pair of brackets includes a base member and a pair of legs extending therefrom and terminating at said one end of the bracket.

22. The articulator as set forth in claim 19 wherein said pair of brackets are configured as mirror images of one another.

23. The articulator as set forth in claim 22 wherein each bracket of said pair of brackets includes a base member and a pair of legs extending therefrom and terminating at said one end of the bracket.

24. The articulator as set forth in claim 13 including a stalk disposed intermediate each said ball and the respective one of said pair of brackets.

25. The articulator as set forth in claim 13 wherein each said bracket of said pair of brackets includes a base member and wherein each of said balls is laterally displaced of the longitudinal axis defined by said base member of the respective one of said pair of brackets.

26. The articulator as set forth in claim 25 including a pair of legs extending from said base member and terminating at said one end of the bracket.

27. The articulator as set forth in claim 26 wherein said brackets of said pair of brackets are configured as mirror images of one another.

28. The articulator as set forth in claim 24 wherein each said bracket of said pair of brackets includes a base member for supporting one of said stalks.

29. The articulator as set forth in claim 28 wherein each said stalk is angled with respect to said bracket to displace said ball laterally of the longitudinal axis of said base member.

30. The articulator as set forth in claim 29 wherein said pair of brackets are configured as mirror images of one another.

31. The articulator as set forth in claim 30 wherein said pivoting means attendant said brackets is formed as an integral part of said brackets.

32. The articulator as set forth in claim 31 wherein said pair of brackets and said pivoting means are formed as an integral one part unit.

33. The articulator as set forth in claim 32 wherein each said ball is disposed longitudinally off center along said base member.

34. The articulator as set forth in claim 32 wherein each said ball is disposed longitudinally centered along said base member.

35. The articulator as set forth in claim 34 wherein said pair of brackets are configured as duplicates of one another.

* * * * *